(12) United States Patent
Pinsonneault et al.

(10) Patent No.: US 8,099,339 B1
(45) Date of Patent: Jan. 17, 2012

(54) SYSTEMS AND METHODS FOR PHARMACY INVENTORY MANAGEMENT

(75) Inventors: Roger Pinsonneault, Alpharetta, GA (US); Matt McGrath, Roswell, GA (US)

(73) Assignee: McKesson Financial Holdings Limited, Hamilton (BM)

( * ) Notice: Subject to any disclaimer, the term of this patent is extended or adjusted under 35 U.S.C. 154(b) by 340 days.

(21) Appl. No.: 12/263,747

(22) Filed: Nov. 3, 2008

(51) Int. Cl.
  *G06Q 10/00* (2006.01)
  *G06Q 40/00* (2006.01)
  *G06Q 20/00* (2006.01)
  *G06G 1/14* (2006.01)
(52) U.S. Cl. .................. 705/28; 705/4; 705/22
(58) Field of Classification Search .......... 705/4, 22, 705/28
  See application file for complete search history.

(56) References Cited

U.S. PATENT DOCUMENTS

| | | | |
|---|---|---|---|
| 5,883,370 A * | 3/1999 | Walker et al. | 235/375 |
| 6,529,801 B1 * | 3/2003 | Rosenblum | 700/237 |
| 6,766,218 B2 * | 7/2004 | Rosenblum | 700/235 |
| 2002/0032582 A1 * | 3/2002 | Feeney, Jr. et al. | 705/2 |
| 2004/0230502 A1 * | 11/2004 | Fiacco et al. | 705/28 |
| 2009/0319293 A1 * | 12/2009 | Lee et al. | 705/2 |
| 2009/0326975 A1 * | 12/2009 | Hardaway et al. | 705/2 |

OTHER PUBLICATIONS

Wermes, Mark K. Knowing claims switches can simply your life. Drug Store News. p. 70. Nov. 23, 1992.*
Svuem Jerry. 340B: A new niche for pharmacy. Drug Topics. Oradell: Dec. 16, 2002. vol. 146, Iss. 23; p. 28, 1 pgs.*

* cited by examiner

*Primary Examiner* — Scott Zare
(74) *Attorney, Agent, or Firm* — Sutherland Asbill & Brennan LLP

(57) ABSTRACT

Systems and methods for tracking prescription drug inventory of a pharmacy at a switch. Embodiments of the invention include receiving, at a switch, a prescription claim transaction from a pharmacy system, where the prescription claim transaction indicates an amount of a drug, and transmitting the prescription claim transaction to a payer system for adjudication. An adjudicated response for the prescription claim is then received from the payer system, and an inventory amount associated with the drug maintained by the switch is updated by the switch. When a determination is made that the inventory amount has met a threshold value, a message is transmitting indicating that the inventory amount has met the threshold value. In some embodiments of the invention the message is sent to the pharmacy or directly to a supplier as part of an order for additional inventory of the drug.

24 Claims, 5 Drawing Sheets

SYSTEMS AND METHODS FOR PHARMACY INVENTORY MANAGEMENT

FIELD OF THE INVENTION

Embodiments of the invention relate generally to prescription claim processing, and more particularly to systems and methods for tracking and/or auditing drug inventory during prescription claim processing.

BACKGROUND OF THE INVENTION

Traditionally, pharmacies have used inventory management software installed at the pharmacy to track the amount of a particular drug product (e.g., prescription medication, medical device, etc.) that has been disbursed and how much remains at the pharmacy. This information is used to determine when to order more supply of a particular drug and to track the disbursement of drugs to patients. While pharmacies have relied on such inventory management software to track their drug supply, these systems are costly to install and maintain at a pharmacy or for a chain of pharmacies. Moreover, such inventory management software information is often only accessible by the pharmacy and is dependent on the pharmacists' (or their agents or employees) entry of disbursement information in the inventory management software system and is therefore susceptible to error, fraud, and abuse with no external oversight.

The risk for fraud and abuse rises when the drugs being prescribed are controlled substances or scheduled drugs. Scheduled drugs are those drugs classified in one of five schedules as determined by the Controlled Substances Act (CSA). The five schedules are categories separated by the abusive and/or addictive nature of the drug and include:

Schedule I—a category of drugs not considered legitimate for medical use (e.g., heroin, lysergic acid diethylamide (LSD), etc.)

Schedule II—a category of drugs considered to have a strong potential for abuse or addiction but that also have legitimate medical use. (e.g., opium, morphine, etc.)

Schedule III—a category of drugs that have less potential for abuse or addiction than Schedule I or II drugs and have a useful medical purpose (e.g., short-acting barbiturates and amphetamines, etc.)

Schedule IV—a medically useful category of drugs that have less potential for abuse or addiction than those of Schedules I, II, and III (e.g., diazepam and chloral hydrate, etc.)

Schedule V—a medically useful category of drugs that have less potential for abuse or addiction than those of Schedules I through IV (e.g., anti-diarrhea medication, etc.).

For such controlled substances as well as other prescription drugs, the Food and Drug Administration (FDA) is placing an increasing emphasis on Risk Minimization Action Plans (RiskMAPs) at the point of granting drug product approvals. A RiskMAP is a strategic safety program designed to meet specific goals and objectives in minimizing known risks of a product while preserving its benefits. A RiskMAP targets one or more safety-related health outcomes or goals and uses one or more tools to achieve those goals. A RiskMAP may incorporate a plan for controlling and closely monitoring drug inventories and drug supply ordering. However, when it comes to drug inventory management, many pharmacies participate in an open distribution model where there are an unlimited number of wholesalers distributing product and pharmacy providers dispensing product. This open distribution model does not support product distribution and product dispensing controls and monitoring that are needed for high risk drug products where the use of RiskMAPs are desirable. Other pharmacies manage their drug product inventory by a limited distribution model where product distribution and dispensing is limited to a contract network of participants. What is needed is a way to provide cost effective drug inventory management to a pharmacy while providing better control and monitoring of drug product inventory without limiting patient access or distribution timeliness.

BRIEF DESCRIPTION OF THE INVENTION

According to an embodiment of the invention, there is disclosed a method for tracking prescription drug inventory at a switch that includes receiving, at a switch, a prescription claim transaction from a pharmacy system, wherein the prescription claim transaction indicates an amount of a drug. The method also includes transmitting the prescription claim transaction to a payer system for adjudication, and receiving an adjudicated response for the prescription claim, where the adjudicated response indicates payment associated with the prescription claim. The method further includes updating an inventory amount associated with the drug, where the inventory amount is maintained by the service provider. The method further includes determining that the inventory amount has met a threshold value, and transmitting a message indicating that the inventory amount has met the threshold value.

In accordance with one aspect of the invention, the method further includes subsequent to determining that the inventory amount has met a threshold value, transmitting an order for additional supply of the drug to a drug supplier. According to another aspect of the invention, receive a notification that the order for additional supply of the drug has been fulfilled by the drug supplier. In accordance with one aspect of the invention, transmitting a message indicating that the inventory amount has met the threshold value includes transmitting a message that requests approval for ordering additional supplies of the drug supplier. According to another aspect of the invention, the drug is a controlled substance. In accordance with one aspect of the invention, updating an inventory amount associated with the drug includes decrementing the inventory amount by an amount of drug dispensed, where the amount dispensed is included in the prescription claim transaction.

According to another aspect of the invention, updating an inventory amount associated with the drug includes incrementing the inventory amount by an amount of drug indicated in the prescription claim transaction, where the prescription claim transaction is a reversal transaction. In accordance with one aspect of the invention, the method includes capturing inventory information for reporting and generating a report of inventory amount updates for the drug that occur over a period of time. According to another aspect of the invention, verifying identification information associated with the pharmacy, physician, or patient prior to transmitting the prescription claim transaction to a payer system for adjudication, where the identification information is included in the prescription claim transaction. In accordance with one aspect of the invention, prior to transmitting the prescription claim transaction to a payer system for adjudication, validating that a quantity dispensed value included in the prescription claim transaction satisfies an expected value associated with the drug. According to yet another aspect of the invention, determining that the inventory amount has met a threshold value comprises determining that the inventory amount has reached or gone beyond a threshold value (e.g., equaling the threshold value or falling below the threshold value).

In accordance with another embodiment of the invention, there is disclosed a system for tracking prescription drug inventory that includes a memory for storing computer-executable instructions, and a processor in communication with the memory. The processor is configured to execute the computer-executable instructions to receive, at a switch, a prescription claim transaction from a pharmacy system, where the prescription claim transaction indicates an amount of a drug. The processor is also configured to execute the computer-executable instructions to transmit the prescription claim transaction to a payer system to receive an adjudicated response for the prescription claim, where the adjudicated response indicates payment associated with the prescription claim, and the processor is configured to execute the computer-executable instructions to update an inventory amount associated with the drug, where the inventory amount is maintained by the service provider. The processor is further configured to execute the computer-executable instructions to determine that the inventory amount has met a threshold value, and transmit a message indicating that the inventory amount has met the threshold value.

According to one aspect of the invention, the processor is further configured to execute instructions to transmit an order for additional supply of the drug to a drug supplier subsequent to determining that the inventory amount has met a threshold value. In accordance with another aspect of the invention, the processor is further configured to execute instructions to receive a notification that the order for additional supply of the drug has been fulfilled by the drug supplier. According to yet another aspect of the invention, the computer-executable instructions to transmit a message indicating that the inventory amount has met the threshold value include transmitting a message that requests approval for ordering additional supplies of the drug supplier. In accordance with another aspect of the invention, the drug is a controlled substance. According to yet another aspect of the invention, the computer-executable instructions to update an inventory amount associated with the drug includes decrementing the inventory amount by an amount of drug dispensed, where the amount dispensed is included in the prescription claim transaction.

In accordance with another aspect of the invention, the computer-executable instructions to update an inventory amount associated with the drug includes incrementing the inventory amount by the amount indicated from a prescription claim reversal request, where the amount may be determined by matching the prescription claim reversal request to a corresponding prescription claim. According to yet another aspect of the invention, the processor is further configured to execute instructions to capture inventory information associated with the drug and generate a report of inventory amount updates for the drug that occur over a period of time. In accordance with another aspect of the invention, the processor is further configured to execute instructions to verify identification information associated with the pharmacy, physician, or patient prior to transmitting the prescription claim transaction to a payer system for adjudication, where the identification information is included in the prescription claim transaction. According to yet another aspect of the invention, the processor is further configured to execute instructions prior to transmitting the prescription claim transaction to a payer system for adjudication. As an example, the processor may validate that a quantity dispensed value included in the prescription claim transaction satisfies an expected value associated with the drug. In accordance with another aspect of the invention, the computer-executable instructions to determine that the inventory amount has met a threshold value comprises determining that the inventory amount has reached or gone beyond a threshold value (e.g., equaling the threshold value or falling below the preset threshold value).

DETAILED DESCRIPTION OF EMBODIMENTS OF THE INVENTION

Figure 1:
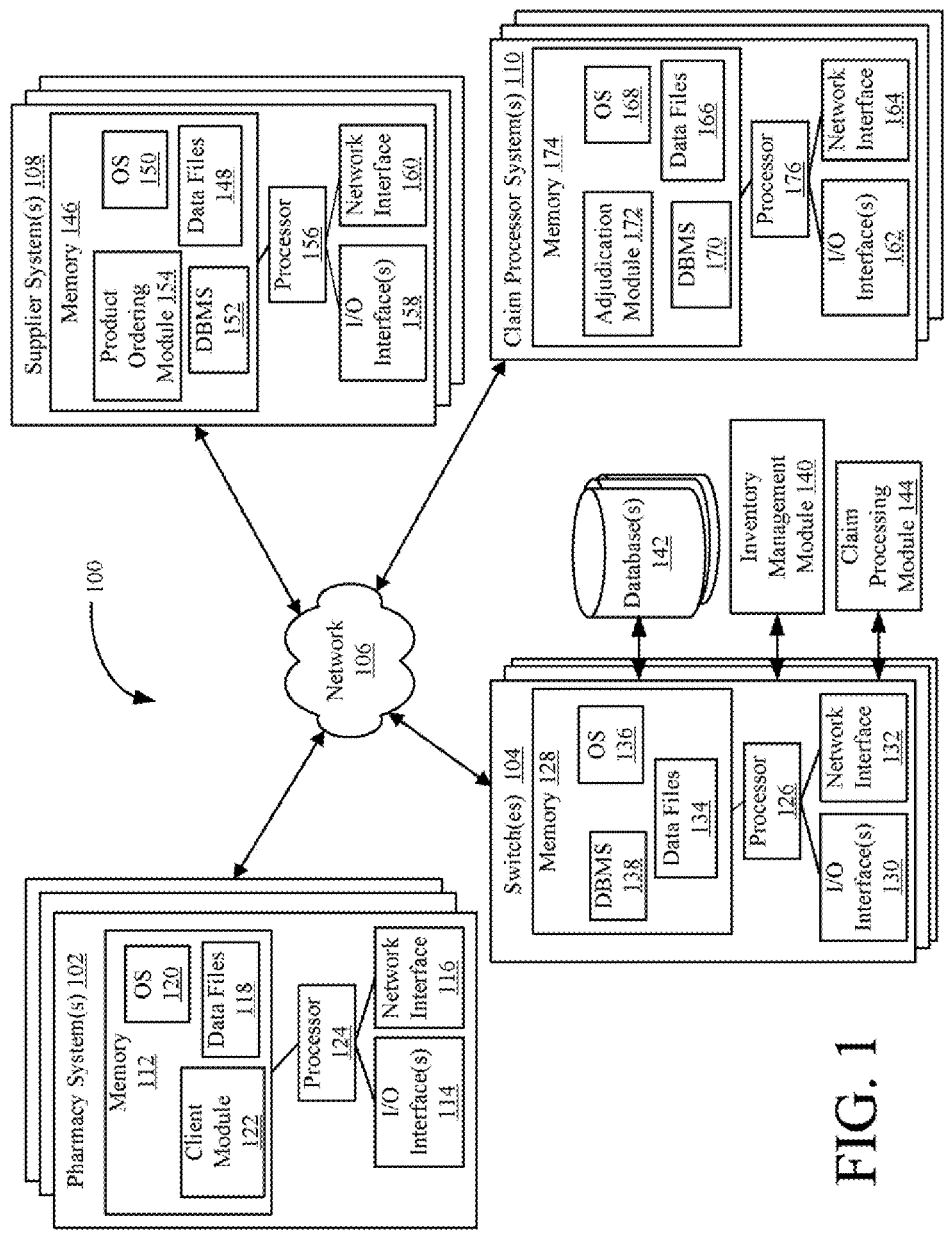
FIG. 1 shows a system for tracking the inventory of a prescription drug at a switch in accordance with an example embodiment of the invention.

Embodiments of the invention are directed to using prescription claim and prescription claim reversal transactions to determine when a pharmacy needs to order medical products (e.g., prescription medications, medical devices, etc.) and places the order on their behalf. In one example embodiment of the invention a switch routing prescription claim transactions receives an adjudicated prescription claim from the payer system, and an inventory amount that is associated with the drug product specified in the adjudicated prescription claim and maintained by the switch is updated by the switch based on the amount of drug dispensed for the transaction associated with the adjudicated claim. When a determination is made that the inventory amount has met a threshold value (e.g., the inventory amount has reached or fallen below a threshold value), a message is transmitted to the pharmacy and/or directly to a supplier as part of an order for additional inventory of the drug. The switch determines when a product order request should occur and initiates the request on behalf of the pharmacy. Embodiments of the invention become an alternative to the pharmacy placing the order either manually or via an inventory management system, either standalone or integrated into the pharmacy's practice management software.

The systems and methods described herein may provide several advantages over traditional drug inventory management solutions including allowing a switch to become a single point of product ordering (i.e. inventory management) and demand (i.e. prescription claims) all through the prescription claim transaction process and providing the ability to monitor for fraud and abuse in the disbursement of prescription drugs. Embodiments of the invention also provide increased product distribution and product dispensing controls over drug inventories (especially for high risk drug products) without overly limiting patient access or causing delay in the distribution of inventory. While the embodiments of the invention discussed herein describe inventory management of prescription drug products, embodiments of the invention are also contemplated to provide inventory management of other medications, medical devices, and other medical products utilized by healthcare providers that are implemented in ways substantially similar to the embodiments of the invention described herein related to the inventory management of drug products.

Embodiments of the invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Embodiments of the invention are described below with reference to block diagrams and flowchart illustrations of systems, methods, apparatuses and computer program products. It will be understood that each block of the block diagrams and flowchart illustrations, and combinations of blocks in the block diagrams and flowchart illustrations, respectively, can be implemented manually and/or by computer program instructions. With respect to computer program instructions, they may be loaded onto a general purpose computer, special purpose computer such as a switch, or other programmable data processing apparatus to produce a machine, such that the instructions which execute on the computer or other programmable data processing apparatus create means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including instruction means that implement the function specified in the flowchart block or blocks. The computer program instructions may also be loaded onto a computer or other programmable data-processing apparatus to cause a series of operational elements or steps to be performed on the computer or other programmable apparatus to produce a computer-implemented process such that the instructions that execute on the computer or other programmable apparatus provide elements or steps for implementing one or more functions specified in the flowchart block or blocks.

Accordingly, blocks of the block diagrams and flowchart illustrations may support combinations of means for performing the specified functions, combinations of elements or steps for performing the specified functions, and program instruction means for performing the specified functions. It will also be understood that each block of the block diagrams and flowchart illustrations, and combinations of blocks in the block diagrams and flowchart illustrations, can be implemented manually or by special purpose hardware-based computer systems that perform the specified functions, elements or steps, or combinations of special purpose hardware and computer instructions.

According to an example embodiment of the invention, there may be a system and method for monitoring drug product inventory during the routing and/or adjudication of prescription claim transactions. Prescription claim transactions are electronic records or messages intended to facilitate the communication of prescription information. For example, prescription claim transactions are intended to communicate prescription claim data between pharmacies (i.e., providers) and payers. Although prescription claim transactions will be discussed hereinafter, it should be understood that the various systems and method of the invention may be practiced in connection with other types of transactions. The content and format of a prescription claim may vary depending on which standard or protocol is used. In general, however, prescription claim transactions may identify at least the intended payer recipient, the drug product to be dispensed, e.g., by National Drug Code number ("NDC number"), the quantity to be dispensed and the days supply, whether the prescription claim relates to a new prescription or a refill prescription, and billing-related information.

FIG. 1 shows a system for tracking the inventory of a prescription drug product at a switch in accordance with an example embodiment of the invention. The overall drug inventory management system 100 of FIG. 1 may include pharmacy systems 102 (e.g., pharmacy practice management systems, hospital or clinic computer systems such as clinical, practice management, scheduling and/or e-prescribing systems, and the like), one or more switches 104, one or more supplier systems 108 (e.g., a drug wholesaler, manufacturer, distributor, corporate warehouse, or other drug product supplying entity), and one or more claim processor systems 110 (e.g., insurance programs, government funded programs, benefits managers, drug manufacturers, other vendors and/or business associates of healthcare service providers, government and/or non-government entities providing financial and/or administrative services, and the like).

Each pharmacy system 102, switch 104, supplier system 108, and/or claim processor system 110 may be configured for accessing and reading associated computer-readable media having stored thereon data and/or computer-executable instructions for implementing the various methods in accordance with example embodiments of the invention. Generally, network devices and systems, including one or more pharmacy systems 102, switches 104, wholesaler systems 108, and claim processor systems 110 have hardware and/or software for transmitting and receiving data and/or computer-executable instructions over a communications link and a memory for storing data and/or computer-executable instructions. These network devices and systems may also include a processor for processing data and executing computer-executable instructions, as well as other internal and peripheral components that are well known in the art. As used herein, the term "computer-readable medium" describes any form of memory or a propagated signal transmission medium. Propagated signals representing data and computer-executable instructions are transferred between network devices and systems.

Prescription claim transactions may be transmitted from the pharmacy system 102 to the switch 104 in batch, real-time or near real-time. A pharmacy system 102 can connect to the switch 104 through a variety of methods, including dial-up, frame relay or leased-line. In an example embodiment of the invention, the entire system may be supported by redundant software, communications links, and uninterruptible power supplies, thereby ensuring that all connections will provide reliable, continuous operation. The overall drug inventory management system 100 also ensures that all of submitted claim transactions are routed quickly, accurately, and consistently.

The pharmacy system 102 may comprise any processor-driven device, such as a personal computer, laptop computer, handheld computer, and the like. The pharmacy system 102 may be located at a standalone pharmacy, a pharmacy associated with a chain of pharmacies, or may be located at (or otherwise associated with) a hospital, physician's office, clinic, or another type of healthcare provider. In addition to having a processor 124, the pharmacy system 102 may further include a memory 112, input/output ("I/O") interface(s) 114 and a network interface 116. The memory 112 may store data files 118 and various program modules, such as an operating system ("OS") 120 and a client module 122. The client module 122 may include an Internet browser or other software, including a dedicated program, for interacting with the switch 104 via a web portal accessible through the web browser or via other communication means. For example, a user such as a pharmacist or their agent (e.g., pharmacy technician, nurse, assistant, office clerk, etc.) or another prescribing entity may utilize the client module 122 to communicate with the switch 104. The client module 122 may also be able to communicate with the supplier system 108, and/or the claim processor system 110.

Still referring to the pharmacy system 102, the I/O interface(s) 114 may facilitate communication between the processor 124 and various I/O devices, such as a keyboard, mouse, printer, microphone, speaker, monitor, bar code readers/scanners, RFID readers, and the like. The network interface 116 may take any of a number of forms, such as a network interface card, a modem, a wireless network card, and the like. These and other components of the pharmacy system 102 will be apparent to those of ordinary skill in the art and are therefore not discussed in more detail herein.

The switch 104 may comprise any processor-driven device that is configured for receiving, processing, and fulfilling prescription claim and prescription claim reversal transactions for adjudication and/or other drug-related requests from the pharmacy system 102, the supplier system 108, and/or claim processor systems 110. The switch 104 may include a processor 126, a memory 128, input/output ("I/O") interface(s) 130, and a network interface 132. The memory 128 may store data files 134 and various program modules, such as an operating system ("OS") 136 and a database management system ("DBMS") 138. In an example embodiment of the invention, the switch 104 provides the web portal functionality accessible by the client module 122 of the pharmacy system 102. In an example embodiment of the invention, the switch 104 receives, processes, and responds to prescription related requests from the client module 122 of the pharmacy system 102, and further receives, processes, and responds to requests and claims received from the adjudication module 172 of claim processor system 110 and/or the product ordering module 144 of the supplier system 108.

In an example embodiment of the invention, a user of the pharmacy system 102 creates and submits prescription claim transactions via a user interface to the switch 104. In example embodiments of the invention, prescription transactions may originate via traditional prescription claim processing or via web portal reporting. According to one embodiment of the invention, the pharmacy system submits prescription claim and/or prescription claim reversal requests through the switch 104. The switch identifies prescription claim (or claim reversal) requests for a particular drug (e.g., a particular NDC number, transaction code, product or service identifier, date of service etc.) from the received claim and delivers the prescription claim requests (or claim reversals) to the claim processing module 144 and then to the claims processor system 110. In an example embodiment of the invention, upon receiving a prescription transaction, the switch 104 may also ensure that the identity and/or authority of the patient, physician, and/or pharmacist are verified. Once the prescription claim transaction has been adjudicated by the claims processor system 110, the switch may be notified and then update how the adjudicated transaction affects drug product inventory levels for the pharmacy, and/or communicate a product order request to a supplier system 108.

In an alternative embodiment of the invention, the pharmacy may access the switch 104 via a web portal where the switch 104 may ensure that the identity and/or authority of the patient, physician, and/or pharmacist are verified and communicate a drug product order request to the supplier system 108. In another alternative embodiment of the invention, the web portal access to the switch 104 may be used by the pharmacist as an alternative to using the pharmacy's practice management system to report product dispensing activity. For example, expiration of a stored drug product, theft, damage, destruction, contamination, or other events than may cause a change to the inventory level of a drug product that would not be reflected in a prescription claim (or reversal) transaction. In another embodiment of the invention, the web portal access to the switch 104 may be used to provide overrides, dummy claim transactions, or system parameter adjustments through controls accessible via the web portal interface to account for inventory events that are not captured by the processing of prescription claim transactions.

It will be appreciated that FIG. 1 has been provided for illustrative purposes only, and that other variations are available in accordance with example embodiments of the invention. For example, the switch 104 may be comprised of two or more distinct switches (also referred to as switch providers) that are in communication with each other. Although not illustrated in FIG. 1, in an example embodiment of the invention, one switch may be operative with one set of pharmacy systems, claim processor systems, and/or supplier systems while another switch may be operative with another set of pharmacies, claim processor systems, or supplier systems. However, each switch may have a data processing arrangement with the other switch(es). Under a data processing agreement, one switch may have direct access to one or more services, including those provided by the modules of another switch, or the switch may have direct access to third party systems accessible through another switch (e.g., claim processor systems, supplier systems, etc.). Under such an arrangement, a switch may also be permitted to obtain services from such entities via the other switch(es).

In an example embodiment of the invention, a claim processing module 144 may receive, process, and respond to requests and claim responses received from the client modules 122 of one or more pharmacy systems 108 or the adjudication module 172 of one or more claim processor systems. In an example embodiment of the invention, the claim processing module 144 may include a back-end analytic, editing, messaging, and reporting system for transactions between pharmacies and claim processors.

The claims processing module 144 validates prescription claim transactions as they pass through the switch 104. In an example embodiment of the invention, the claims processing module 144 may include a business rules engine that interfaces with the database 142, where the database 142 may contain registration data to validate physician, patient, and pharmacy participation. The claim processing module 144 may issue denial messages to the pharmacy system 102 when patient, physician, and/or pharmacy identification and/or authorization data contained in a prescription claim transaction is not verified. If the patient, physician, and/or pharmacy registration data is verified then the prescription claim transaction is routed from the switch 104 to the claim processor system 110 associated with the prescription claim transaction so the prescription claim transaction may be adjudicated by the claim processor system 110.

In an alternative embodiment of the invention, as an additional check for fraud, abuse, or error for particular drugs, the claims processing module 144 may also validate a ratio of the "Quantity Dispensed" to the "Days Supply" that is specified in the prescription claim transaction. The claims processing module 144 may communicate a prescription claim request denial to the pharmacy system 108 if the "Quantity Dispensed"/"Days Supply" ratio meets an identified threshold.

Once adjudication has been completed at the claim processor system 110 a response message corresponding to the prescription claim transaction is sent back to the switch 104 and the claim processing module 144. The claim processing module 144 identifies all approved (e.g., "Paid", "Duplicate of Paid", or "Captured" for prescription claim transactions and "Accepted" for prescription claim reversals), and those adjudicated transactions (i.e., approved claims and reversals) are then presented to the inventory management module 140 for drug inventory processing.

The inventory management module 140 may include a back-end analytic, editing, messaging, and reporting system for transactions between prescribing entities, pharmacies, and wholesalers. The inventory management module 140 allows a pharmacy system 102 to automatically order a particular drug product (or additional inventory of a drug product) via the submission of prescription claim transactions to the switch 104. The inventory management module 140 reconciles prescription claim transaction data to determine when a product order is necessary. In an example embodiment of the invention, the inventory management module 140 maintains a perpetual "on hand" inventory value for a particular drug supply at a particular pharmacy. In an example embodiment of the invention, the inventory management module 140 may "net out" prescription claims and reversals on a daily basis. That is, the approved prescription claim transaction may decrement the "on hand" inventory value, while the claim reversal transaction may increment the "on hand" inventory value for a particular drug supply at a particular pharmacy. The inventory management module 140 may then compare the "netted out" activity for a particular drug supply with a particular pharmacy to a stored threshold value associated with the "on hand" inventory to determine if a product order transaction is required. In an example embodiment of the invention, the inventory management module 140 may initiate a product order transaction if the "on-hand" inventory is equal to (or less than) a threshold value of "1". In another example embodiment of the invention, the threshold value may be set to "0". The threshold may be set at other values appreciable by one of ordinary skill in the art.

When a drug inventory has met the threshold value (e.g., equaling the threshold value or falling below the threshold value), the inventory management module 140 may create daily drug product order files for each wholesaler. In an example embodiment of the invention, the inventory management module 140 may create one consolidated product order file per supplier and send that product order file to the wholesaler. In an example embodiment of the invention, the product order file may be automatically created and sent to the supplier once the inventory level for a particular drug has reached or gone beyond a preset threshold value (e.g., equaling the threshold value or falling below the threshold value), where the threshold value reflects an acceptable level of "on hand" inventory for a particular drug where drug product ordering is unnecessary. In an alternative embodiment, a message may be created and sent to the pharmacy system 102 contemporaneously with the delivery of the product order file to the supplier system 108, or a message may be created and sent to the pharmacy system 102 for approval of the product ordering prior to the product order file being sent to the supplier system 108.

For example, if the inventory management module 140 receives an approved adjudicated prescription claim transaction for Drug X, 20 mgs, 30 tablets, then it is assumed that because it is paid by the processor that the pharmacy is going to dispense the medication and the inventory is going to be decremented by 30 tablets. However, if an approved adjudicated prescription claim transaction is received and then a reversal transaction is submitted for the same Drug X, 20 mgs, 30 tablets, then essentially, the reversal is going to increment the inventory by the amount indicated in the reversal medication because it is assumed the medication is not dispensed. In an example embodiment of the invention, the inventory management module 140 may "net out" prescription claims and reversals on a daily basis, and the drug product order may be created once that process has completed and an inventory replenishment for a particular drug has been indicated based on the inventory amount reaching or going beyond a preset threshold value (e.g., equaling the preset threshold value or falling below the preset threshold value). In an example embodiment of the invention, overrides, dummy claim transactions, or system parameter adjustments through controls accessible via a web portal interface may be used to account for inventory events that are not captured by the processing of prescription claim transactions (e.g., expiration of a stored drug product, theft, damage, destruction, contamination, or other events than may cause a change to the inventory level of a drug product that would not be reflected in a prescription claim (or reversal) transaction).

Various reports may be generated and/or accessible at the switch 104 that utilize data managed by the inventory management module 140. Some reports may provide an audit of a pharmacy's inventory for particular drugs such as controlled substances susceptible to abuse to monitor for any cases of fraud, abuse, or error. These reports may be used by the third parties or government agencies to monitor and police the disbursement of certain medications that could be abused. Other reports may provide a manufacturer of a particular drug information about how often a particular drug is being prescribed or how often additional inventory of a particular drug is ordered, etc.

The inventory management module 140 and the claim processing module 144 may be in communication with, but separate from, the switch 104, or alternatively, the inventory management module 140 and the claim processing module 144 may be incorporated into the switch 104. In one example embodiment of the invention, the inventory management module 140 and the claim processing module 144 may also be in communication with each other either electronically, or in an alternative embodiment, data may be provided between the two modules manually. In alternative embodiments of the invention, the inventory management module 140 and claim processing module 144 may be consolidated into one module that performs the functions of both modules. A more detailed discussion of the functionality of the inventory management module 140 and the claim processing module 144 is included below in the discussion of FIGS. 2-4.

As described herein, the switch 104 may comprise computer-executable instructions for implementing one or more methods described herein, including processing, editing and/or routing prescription claim transactions, updating drug inventories associated with the prescription claim transactions, and ordering drug product supplies once the inventory has reached or gone beyond a particular threshold value for that drug product (e.g., equaling the threshold value or falling below the threshold value). The switch 104 may likewise be operative to store prescription data, patient data, pharmacy data, a listing of drug inventory information for various drug products, etc. in database(s) 142, which may include a distinct database and/or a database shared with the pharmacy systems 102, the supplier system 108, and/or the claim processor system 110. In an example embodiment of the invention, the database(s) 142 in communication with the switch 104 may include additional data to facilitate drug inventory management and ordering by extracting inventory-related information using prescription claim transactions including: patient, physician, pharmacy, and supplier registration (e.g., identification and/or authorization) information, dosage information ratio for various drug products (e.g., Quantity Dispensed/Days Supply ratios), prescription claim (and reversal) transaction activity history, prescription activity information tracked by patient ID, physician ID, date of service, product service ID, quantity dispensed, or days supply.

The supplier system 108 may include any processor-driven device that is configured for receiving, processing, and fulfilling prescription transactions for drug samples received from the pharmacy systems 102 via the switch 104. The supplier system 108 may include a processor 156, a memory 150, input/output ("I/O") interface(s) 152, and a network interface 154. The memory 150 may store data files 146 and various program modules, such as an operating system ("OS") 148, and the prescription claim module 144. The prescription module 144 may receive, process, and respond to prescriptions received from a pharmacy system 102 via the switch 104 as well as generate claim transactions relating to the filled prescription to be routed to the claim processor system 110 via the switch 104.

In an example embodiment of the invention, the switch 104 may electronically deliver the prescription orders to the supplier systems 108 on an agreed upon schedule (e.g., daily) in a batch format. For instance, in an example embodiment of the invention, the inventory management module 140 may "net out" prescription claims and reversals on a daily basis, and the drug product order may be created once that process has completed and an inventory replenishment for a particular drug has been indicated. In alternative embodiments of the invention, the prescription orders may be delivered on a rolling basis, real-time or otherwise. Upon receipt of an order, the supplier system 108 may prepare the order for next business day delivery to the pharmacy or another delivery process desired by the pharmacy or other entity.

In an example embodiment of the invention, the supplier system 108 to be used to fulfill the drug product order may be designated by the pharmacy to receive the ordered drug product. The designation may be included in the prescription claim transaction, or may be a stored preference at the switch accessible at the time of drug product order creation. In an example embodiment of the invention, the drug product order created may be a drug product order file that includes an NDC number, prescription number, date of service, service/provider identifier. The drug product order file does not need to include patient identification, physician identification, or pharmacy identification other than the service/provider identifier Once a drug product order has been sent from the switch 104 and received at the supplier system 108, the supplier system 108 may send a receipt acknowledgement of the received product order back to the switch 104 to confirm the order is to be processed and for reporting purposes.

The claim processor system 110 may include any processor-driven device that is configured for receiving, processing, and fulfilling requests relating to claim adjudication processing. According to an example embodiment of the invention, the claim processor system 110 may process prescriptions claims received from pharmacy systems 102 via the switch 104. The claim processor system 110 may include a processor 176, a memory 174, input/output ("I/O") interface(s) 162, and a network interface 164. The memory 174 may store data files 166 and various program modules, such as an operating system ("OS") 168, a database management system ("DBMS") 170, and an adjudication module 172. The adjudication module 172 may receive, process, and respond to claims received from the switch 104 indicating approval or denial (in part or in whole) of the prescription claim transaction.

In FIG. 1, a pharmacy system(s) 102, switch 104, supplier system(s) 108 and claim processor system(s) 110 may be in communication with each other via one or more networks 106. The one or more networks 106 may include any telecommunication and/or data network, whether public, private, or a combination thereof, including a public switched telephone network (PSTN), a cellular network, a local area network, a wide area network, an intranet, an Internet, the Internet, intermediate hand-held data transfer devices, and/or any combination thereof and may be wired and/or wireless. The one or more networks 106 may also allow for real-time, off-line, and/or batch transactions to be transmitted between or among the pharmacy system(s) 102, the switch 104, the supplier system(s) 108, and the claim processor system(s) 110. Due to network connectivity, various methodologies as described herein may be practiced in the context of distributed computing environments.

Those of ordinary skill in the art will appreciate that the system 100 shown in and described with respect to FIG. 1 is provided by way of example only. Numerous other operating environments, system architectures, and device configurations are possible. Accordingly, embodiments of the invention should not be construed as being limited to any particular operating environment, system architecture, or device configuration.

Figure 2:
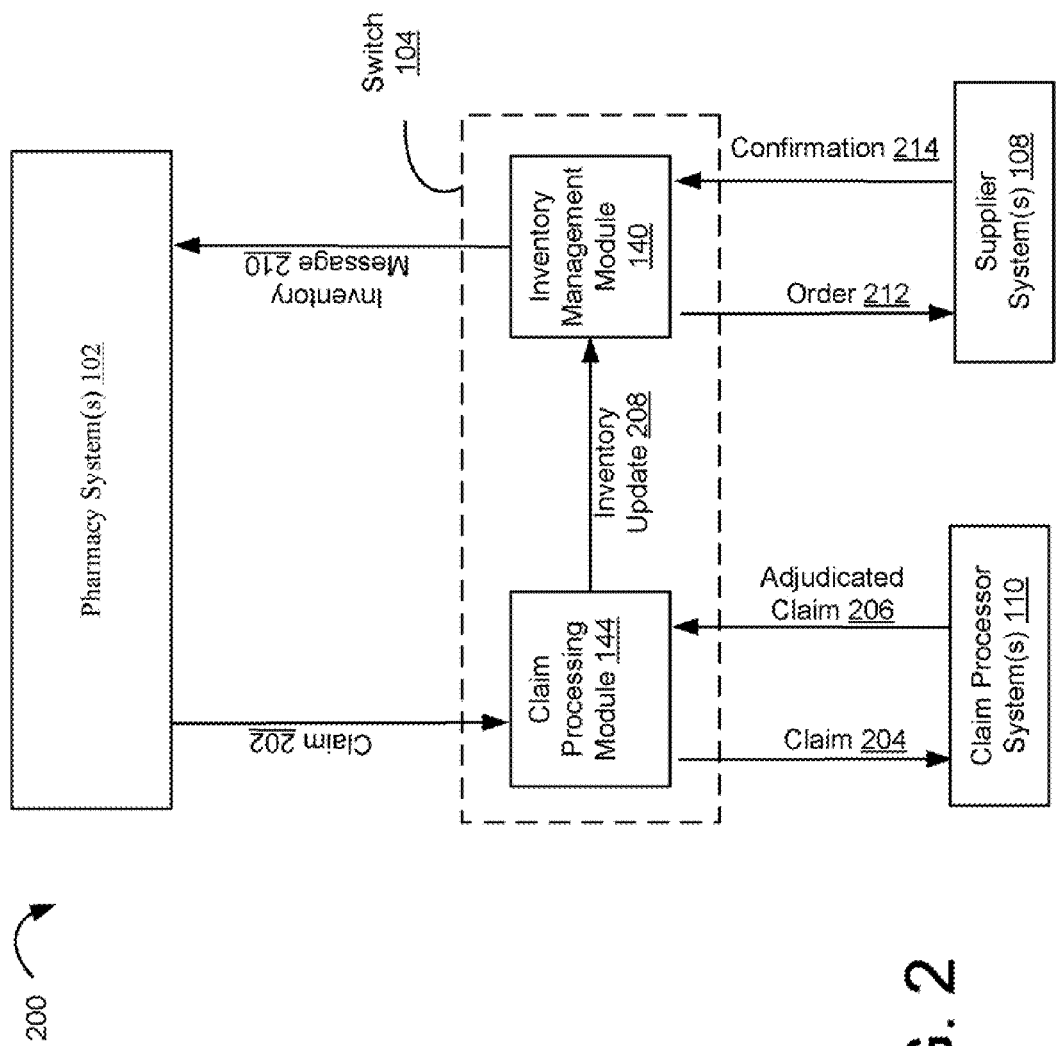
FIG. 2 shows a data flow between the entities of the system for tracking the inventory of a prescription drug at a switch in accordance with an example embodiment of the invention.

FIG. 2 shows a data flow 200 between the entities of the system for tracking the inventory of a prescription drug at a switch in accordance with an example embodiment of the invention. As shown in FIG. 2, once the pharmacy receives a prescription script from the patient or directly from a clinician's office, the pharmacy system 102 creates a claim (claim 202) corresponding to the prescription to be adjudicated by the claim processor system 110. The prescription claim or prescription claim reversal (claim 202) is sent from the pharmacy system 102 to the claim processing module 144 via the switch 104 where the claim processing module 144 may simply route claim 202 to the corresponding claim processor system 110, or the claim processing module 144 may perform a variety of edits and review to ensure that claim 202 is in proper format for the corresponding claim processor system 110 as well as edit the claim to contain the appropriate information for proper adjudication. Once the edits (if any) provided by the claim processing module 144 on claim 202 are completed, the claim (claim 204) is routed to the appropriate claim processing system 110.

The claim processing system 110 then adjudicates the claim (or reversal) and indicates the results of the adjudication (e.g., approval or unapproved) in an adjudicated response (adjudicated response 206) that is routed back to the switch 104 and ultimately back to the pharmacy system 102 through the switch 104. The claim processing module 144 may review adjudicated response 206 to update files pertaining to the transaction (e.g., patient eligibility files, transaction records, etc.). The update to the files may include sending information (inventory update 208) to the inventory management module 140 for updating stored inventory data associated with the drug product identified in the adjudicated claim 206. In an example embodiment of the invention, the inventory management module 140 may be in communication with the claim processing module 144 to obtain information for use in the updating of inventory information pertaining to a particular drug product.

In the example embodiment of FIG. 2, the inventory management module 140 and claim processing module 144 are incorporated into the switch 104. In alternative embodiments of the invention, the inventory management module 140 and claim processing module 144 may be separate and distinct from the switch 104 and in communication with the switch 104. In one example embodiment of the invention, the inventory management module 140 and the claim processing module 144 may be in communication with each other either electronically, or in an alternative embodiment, data may be provided between the two modules manually. In alternative embodiments of the invention, the inventory management module 140 and claim processing module 144 may be consolidated into one module that performs the functions of both modules.

Next, the inventory management module 140 updates a database entry reflecting the inventory data for a particular drug based on the approved adjudicated claim (or reversal) 206. A more detailed discussion of the inventory tracking and messaging performed by the inventory management module 140 is described below with reference to FIGS. 3 and 4.

When the inventory management module 140 determines that the drug product inventory has reached a threshold value (e.g., equaling the threshold value or falling below the threshold value), then an inventory message 210 may be created and sent to the pharmacy system 102. In one embodiment of the invention, the inventory message 210 may be consolidated with the adjudicated response 206 and both may be sent to the pharmacy system 102. Either contemporaneously with the inventory message 210 or after the pharmacy system 102 has responded to the inventory message 210, the inventory management module 140 may create an order 212, which requests additional quantity of the drug product from a supplier (e.g., drug wholesaler, distributor, drug manufacturer, corporate warehouse, etc.) system 108. In the embodiment shown in FIG. 2, once the supplier system 108 has processed the order and/or fulfilled the drug product order by sending the ordered drug product to the pharmacy system 102, a confirmation 214 of order receipt and/or fulfillment may be sent to the inventory management module 140.

In alternative embodiments of the invention, it is appreciated that one or more transmissions of a claim, adjudicated response, order, confirmation, or inventory message may bypass the switch 104 (and/or the inventory management module 140 or claim processing module 144) when communicating with the intended entity (e.g., pharmacy system, claim processor system, supplier system, or other third party system). For example, in one embodiment of the invention, the inventory management module 140 of the switch 104 may send the order information to the pharmacy system for approval and the pharmacy system 102 may create and transmit the order 212 to the supplier system 108 bypassing the switch 104 as a result. In another example embodiment of the invention, the supplier system 108 may generate and send the confirmation 214 directly to the pharmacy system 102 either in addition to routing the confirmation 214 to the switch 104, or alternatively, bypassing the switch 104 as a result.

Figure 3:
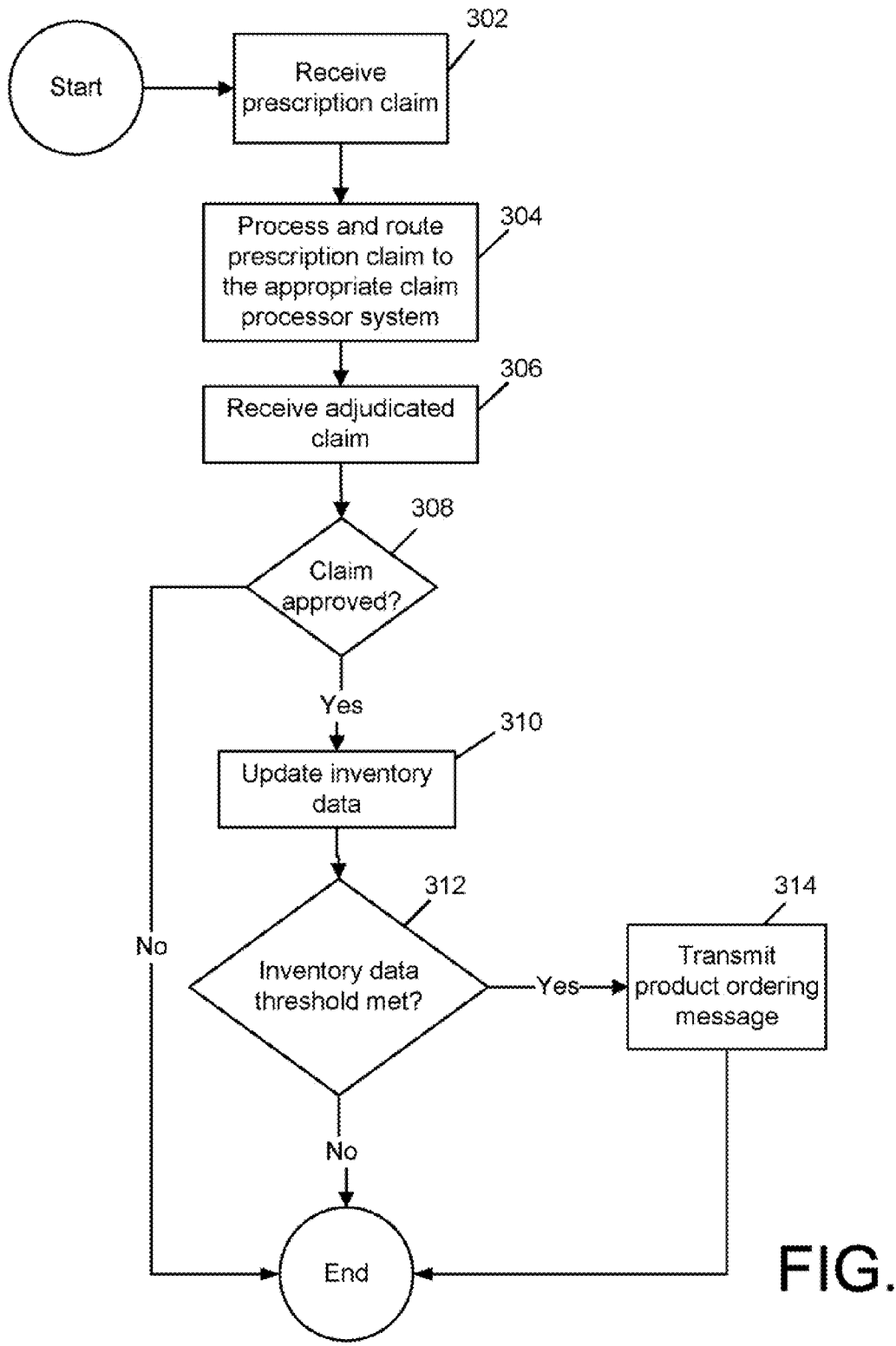
FIG. 3 shows a flowchart of tracking the inventory of a prescription drug at a switch in accordance with an example embodiment of the invention.

FIG. 3 shows a flowchart of tracking the inventory of a prescription drug at a switch in accordance with an example embodiment of the invention. As shown in FIG. 3, the process begins with block 302 where a prescription claim to be adjudicated is provided from a pharmacy to a switch (e.g., new prescription, refill, partial fill, reversal, etc.). The prescription data to be included in the prescription claim transaction may include patient identification information such as a patient first name, patient last name, patient street address, patient state/province code, patient ZIP/postal code, date of birth, and/or patient gender code. The prescription claim data may also include a pharmacy identifier, a physician identifier, an identifier for the medication or equipment (e.g., NDC number), quantity dispensed, the assigned days supply, BIN Number, group number, etc. In some embodiments of the invention, the prescription claim data may include a patient identifying number (e.g., a patient's Cardholder ID) if such an identifier previously exists, though such patient identifying number is not required for rewards processing. In example embodiments of the invention, the transaction standard for the electronic prescription claim submission may be one of National Council for Prescription Drug Programs (NCPDP) Telecommunication Standard, American National Standards Institute (ANSI) X12, Health Level Seven (HL7), or similar transaction standards. Alternatively, the electronic transactions and/or the format of the transactions may be proprietary.

As shown in FIG. 3, in block 302 a pharmacy or other clinician entity creates a claim (or claim reversal) for the filled, or to be filled, prescription and submits the claim for adjudication to the corresponding claim processor (e.g., payer system) via the switch. Next, block 304 is invoked where the switch processes the received claim and routes it to the appropriate claim processor system for adjudication. Once the claim (or reversal) has been adjudicated, block 306 is invoked where an adjudicated response message is sent to, and received by, the switch. The adjudication response message may indicate the results of the claim processor system's adjudication of the claim (or reversal) associated with the prescription. In an example embodiment of the invention, the submission of the claim (or reversal) may occur either before or simultaneously with filling the prescription for the prescribed drug.

Next, block 308 is invoked where the adjudicated claim is reviewed to determine if the adjudicated claim (or adjudicated claim reversal) response indicates that the prescription claim (or reversal) was approved or paid by the claim processor. If the adjudicated claim was not approved or paid by the claim processor, then the inventory management processing may be aborted and a message may be sent to the pharmacy system indicating the adjudicated claim (or adjudicated claim reversal) as not being approved by the claim processor system.

If the adjudicated claim (or adjudicated claim reversal) was approved or paid by the claim processor, then block 310 is invoked to update inventory data associated with the drug specified in the approved adjudicated claim (or approved adjudicated claim reversal). The database entry reflecting the inventory data for a particular drug may be updated based on the approved adjudicated claim (or reversal). In an example embodiment of the invention updating an inventory amount associated with the drug includes decrementing a stored inventory amount by the amount of drug dispensed indicated by the adjudicated claim, or alternatively, updating an inventory amount associated with the drug includes incrementing the inventory amount by the amount of drug indicated in the prescription claim transaction when the prescription claim transaction is a reversal transaction. In one embodiment of the invention, the stored inventory amount may be updated after every approved adjudicated claim associated with a particular drug is processed. In an alternative embodiment of the invention, all of the approved adjudicated claims associated with a particular drug over a period of time may be considered and the collective incrementing or decrementing resulting from reviewing all of those adjudicated claims may then be used to update the stored inventory data associated with a particular drug.

Next, block 312 is invoked where it is determined if the updated inventory amount associated with the drug has reached or gone beyond a threshold value (e.g., drug X has less than Y daily dosages remaining to be dispensed at pharmacy Z). In an example embodiment of the invention, the threshold value may be a preset inventory amount that indicates that the supply of a drug has been decremented to the point that a particular drug supply needs to be replenished. If the threshold value has not been met (e.g., not equaling the threshold value or not falling below the threshold value), then the inventory management process is ended.

If the threshold value has been met, then block 314 is invoked where a product ordering message is created at the switch. In one embodiment of the invention, the product ordering message created at the switch is a notice (e.g., message, report, etc.) to the pharmacy that submitted the corresponding prescription claim transaction that indicates that additional supply of a particular drug should be ordered. In another embodiment of the invention, the product ordering message is sent to the pharmacy that submitted the corresponding prescription claim transaction and the message includes a request approval for the switch to create an order for additional supply of the drug associated with the corresponding prescription claim transaction. In an alternative embodiment of the invention, the product ordering message is appended to the message pertaining to the adjudicated prescription claim transaction sent to the pharmacy by the switch. In another embodiment of the invention the product ordering message created at the switch is an order for a particular drug product to be sent to a supplier on behalf of the pharmacy that submitted the corresponding prescription claim transaction. Additional detail as to the creation and processing of a drug product order at the switch is provided below with reference to FIG. 4. Although not shown in FIG. 3, in an alternative embodiment of the invention, the pharmacy system and/or a third party system may periodically request data relating to the inventory and/or dispensing activities associated with a particular drug, pharmacy, prescriber, patient, etc.

Figure 4:
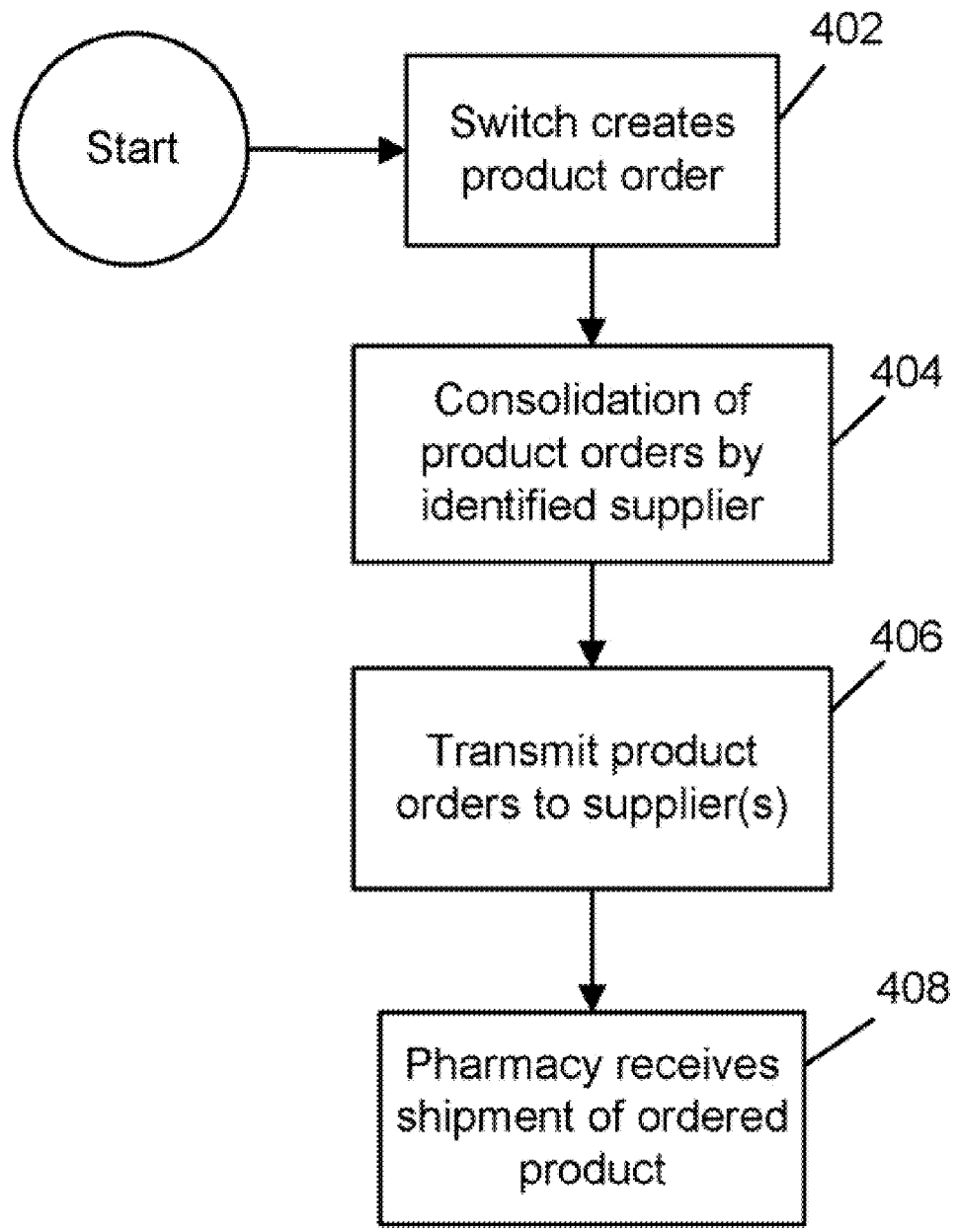
FIG. 4 shows a flowchart of creating and processing drug product orders in accordance with an example embodiment of the invention.

FIG. 4 shows a flowchart of creating and processing drug product orders in accordance with an example embodiment of the invention. As shown in FIG. 4, the drug product order creation and processing begins at block 402 where the switch creates a drug product order. In an example embodiment of the invention, the drug order may specify the pharmacy or other clinician office on whose behalf the switch submitted the order. In an example embodiment of the invention, the amount of drug product ordered may be the amount needed to bring the inventory back to an initial value. In an alternative embodiment, the amount of drug product ordered may be equal to the previous prescription claim transaction or the collective amount of a group of previous prescription claim transactions. Next, block 404 is invoked where the orders for various drug products are consolidated based on the supplier to which the orders are to be sent. This consolidation may occur through the use of batch processing performed periodically or at a set time or set time interval. In an alternative embodiment of the invention, the consolidation of block 404 may be omitted and drug product orders may be sent to a supplier individually in real time.

As shown in FIG. 4, after consolidation, block 406 may be invoked to transmit the drug product orders to the corresponding supplier. Once the supplier processes the orders, block 408 is invoked where the ordered drug products are sent from the supplier to the pharmacy or other clinician office on whose behalf the switch submitted the order.

Figure 5:
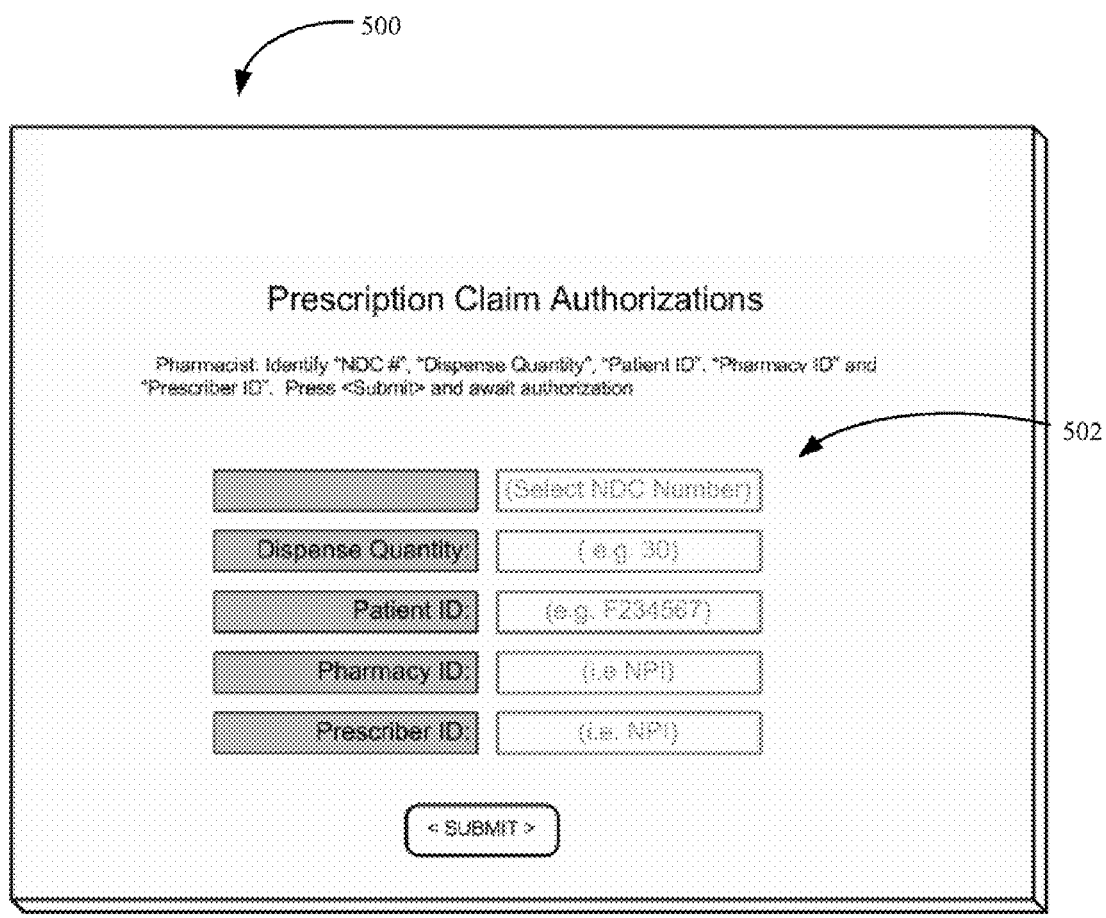
FIG. 5 shows a web portal for use in tracking the inventory of a prescription drug in accordance with an example embodiment of the invention.

FIG. 5 shows a web portal 500 for use in tracking the inventory of a prescription drug in accordance with an example embodiment of the invention. As shown in FIG. 5, a prescription claim may be entered through the user interface 502 presentation via a web portal. In one embodiment of the invention, the web portal 500 may be accessible via a web browser through the pharmacy system or otherwise be available via a computer. As shown in FIG. 5, the information to be entered and included in a prescription claim transaction may include a drug identifier (e.g., NDC Number), dispense quantity, patient identifier, pharmacy identifier, prescriber identifier. Other information useful for routing and/or adjudicating the prescription claim by a switch or payer system not shown in FIG. 5 may also be included in a pharmacy claim transaction and inputted through a user interface via a web portal.

Accordingly, many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of this application. Although specific terms are employed herein, they are used in a generic and descriptive sense only and not for purposes of limitation.

The invention claimed is:

1. A computer implemented method for tracking prescription drug inventory at a prescription claim transaction switch comprising:
   receiving a prescription claim transaction from a pharmacy system associated with a pharmacy, wherein the prescription claim transaction indicates an amount of a drug;
   transmitting the prescription claim transaction to a payer system for adjudication;
   receiving an adjudicated response for the prescription claim transaction, wherein the adjudicated response indicates payment associated with the prescription claim transaction;
   updating, based upon the received adjudicated response indicating the payment, an inventory amount associated with the drug, wherein the inventory amount is maintained by a service provider;
   determining that the inventory amount has met a threshold value; and
   transmitting a message to the pharmacy system indicating that the inventory amount has met the threshold value,
   wherein the prior steps are performed by the prescription claim transaction switch comprising one or more processors executing computer-executable instructions.

2. The method of claim 1, wherein transmitting a message indicating that the inventory amount has met the threshold value comprises transmitting an order for additional supply of the drug to a drug supplier.

3. The method of claim 2, further comprising:
   receiving a notification that the order for additional supply of the drug has been fulfilled by the drug supplier.

4. The method of claim 1, wherein transmitting a message indicating that the inventory amount has met the threshold value comprises transmitting a message that requests approval for ordering additional supplies of the drug supplier.

5. The method of claim 1, wherein the drug is a controlled substance.

6. The method of claim 1, wherein updating an inventory amount associated with the drug includes decrementing the inventory amount by an amount of drug dispensed, wherein the amount dispensed is included in the prescription claim transaction.

7. The method of claim 1, wherein updating an inventory amount associated with the drug includes incrementing the inventory amount by an amount of drug indicated in the prescription claim transaction, wherein the prescription claim transaction is a reversal transaction.

8. The method of claim 1, further comprising:
capturing inventory information for reporting; and
generating a report of inventory amount updates for the drug that occur over a period of time.

9. The method of claim 1, prior to transmitting the prescription claim transaction to a payer system for adjudication, verifying identification information associated with the pharmacy, physician, or patient, wherein the identification information is included in the prescription claim transaction.

10. The method of claim 1, prior to transmitting the prescription claim transaction to a payer system for adjudication, validating that a quantity dispensed value included in the prescription claim transaction satisfies an expected value associated with the drug.

11. The method of claim 1, wherein determining that the inventory amount has met a threshold value comprises determining that the inventory amount has reached or gone beyond a threshold value.

12. The method of claim 1, further comprising transmitting a message to the pharmacy system indicating the prescription claim transaction is being denied based at least in part on the determination of possible fraud.

13. A system for tracking prescription drug inventory comprising:
a memory for storing computer-executable instructions; and
a prescription claim transaction switch comprising one or more processors in communication with the memory, wherein the one or more processors are configured to execute the computer-executable instructions to:
receive, at the prescription claim transaction switch, a prescription claim transaction from a pharmacy system associated with a pharmacy, wherein the prescription claim transaction indicates an amount of a drug;
transmit the prescription claim transaction to a payer system for adjudication;
receive an adjudicated response for the prescription claim transaction, wherein the adjudicated response indicates payment associated with the prescription claim transaction;
update, based upon the received adjudicated response indicating the payment, an inventory amount associated with the drug, wherein the inventory amount is maintained by a service provider;
determine that the inventory amount has met a threshold value; and
determining that a ratio of the inventory amount to a dispensed amount of the drug has met a threshold that indicates possible fraud; and
transmitting a message to the pharmacy system indicating that the inventory amount has met the threshold value.

14. The system of claim 13, wherein the processor is further configured to execute instructions to:
subsequent to determining that the inventory amount has met a threshold value, transmit an order for additional supply of the drug to a drug supplier.

15. The system of claim 14, wherein the processor is further configured to execute instructions to:
receive a notification that the order for additional supply of the drug has been fulfilled by the drug supplier.

16. The system of claim 13, wherein the software instructions to transmit a message indicating that the inventory amount has met the threshold value include transmitting a message that requests approval for ordering additional supplies of the drug supplier.

17. The system of claim 13, wherein the drug is a controlled substance.

18. The system of claim 13, wherein the software instructions to update an inventory amount associated with the drug include decrementing the inventory amount by an amount of drug dispensed, wherein the amount dispensed is included in the prescription claim transaction.

19. The system of claim 13, wherein the software instructions to update an inventory amount associated with the drug include incrementing the inventory amount by an amount of drug indicated in the prescription claim transaction, wherein the prescription claim transaction is a reversal transaction.

20. The system of claim 13, wherein the processor is further configured to execute instructions to:
capture inventory information associated with the drug; and
generate a report of inventory amount updates for the drug that occur over a period of time.

21. The system of claim 13, wherein the processor is further configured to execute instructions to:
prior to transmitting the prescription claim transaction to a payer system for adjudication, verify identification information associated with the pharmacy, physician, or patient, wherein the identification information is included in the prescription claim transaction.

22. The system of claim 13, wherein the processor is further configured to execute instructions to:
prior to transmitting the prescription claim transaction to a payer system for adjudication, validate that a quantity dispensed value included in the prescription claim transaction satisfies an expected value associated with the drug.

23. The system of claim 13, wherein the software instructions to determine that the inventory amount has met a threshold value include determining that the inventory amount has reached or gone beyond a threshold value.

24. The system of claim 13, wherein the processor is further configured to execute instructions to transmit a message to the pharmacy system indicating the prescription claim transaction is being denied based at least in part on the determination of possible fraud.

* * * * *